(12) United States Patent
Liu et al.

(10) Patent No.: US 11,378,570 B2
(45) Date of Patent: Jul. 5, 2022

(54) CYTOTOXICITY TEST METHOD FOR MEDICAL DEVICES

(71) Applicant: Alcon Inc., Fribourg (CH)

(72) Inventors: Xuemei Liu, Fort Worth, TX (US); Fan Zhang, Keller, TX (US); Denise P. Rodeheaver, Fort Worth, TX (US); Ann Marie Wright, Roswell, GA (US); Charlon Tolliver, Fort Worth, TX (US); Jamie Michaelis Walker, Burleson, TX (US); Robert Edward Rose, North Richland Hills, TX (US); Stephen Paul Shannon, Arlington, TX (US); Jeffrey Charles White, Southlake, TX (US)

(73) Assignee: Alcon Inc., Fribourg (CH)

( * ) Notice: Subject to any disclaimer, the term of this patent is extended or adjusted under 35 U.S.C. 154(b) by 811 days.

(21) Appl. No.: 15/988,421

(22) Filed: May 24, 2018

(65) Prior Publication Data
US 2018/0348205 A1    Dec. 6, 2018

Related U.S. Application Data

(60) Provisional application No. 62/510,542, filed on May 24, 2017.

(51) Int. Cl.
| | |
|---|---|
| *G01N 33/50* | (2006.01) |
| *G01N 15/00* | (2006.01) |
| *C12M 1/32* | (2006.01) |
| *C12M 1/34* | (2006.01) |
| *C12N 5/078* | (2010.01) |

(52) U.S. Cl.
CPC ......... *G01N 33/5014* (2013.01); *G01N 15/00* (2013.01); *C12M 1/34* (2013.01); *C12M 23/12* (2013.01); *C12M 41/36* (2013.01); *C12M 41/46* (2013.01); *C12N 5/0634* (2013.01)

(58) Field of Classification Search
CPC .................................................... C12M 41/46
See application file for complete search history.

(56) References Cited

U.S. PATENT DOCUMENTS

| | | | |
|---|---|---|---|
| 5,229,288 | A | 7/1993 | Mori |
| 6,982,152 | B2 | 1/2006 | Riss |
| 7,282,348 | B2 | 10/2007 | Riss |
| 8,480,227 | B2 | 7/2013 | Qiu |
| 9,388,451 | B2 | 7/2016 | Ramachandran |

OTHER PUBLICATIONS

Dutta et al., Invest Ophthalmol Vis Sci., 2016, 57:5616-5624.*
Fellows et al., Mutagenesis, 2011, 26(6):771-781.*
Cresson, Vi-Cell XR instructions, 2006, 1 page.*
Riss TL, Moravec RA, Niles AL, Benink HA, Worzella TJ, Minor L. Cell Viability Assays. In: Sittampalam GS, Coussens NP, Nelson H, Arkin M, Auld D, Austin C, et al., editors. Assay Guidance Manual. Bethesda (MD)2004.
Li W, Zhou J, Xu Y. Study of the in vitro cytotoxicity testing of medical devices. Biomed Rep. 2015;3:617-20.
Mosmann T. Rapid colorimetric assay for cellular growth and survival: application to proliferation and cytotoxicity assays. Journal of immunological methods. 1983;65:55-63.
USP General Chapter <87> Biological Reactivity Tests, In Vitro, 2015.
International Organization for Standardization ISO 10993-5: 2009. Biological evaluation of medical devices—Part 5: Tests for in vitro cytotoxicity.
Japanese Guidelines for Basic Concepts for Evaluating Biological Safety of Medical Devices Required for Application of Manufacturing/Marketing Approval (PFSB/ELD/OMDE Notification No. 0301-20. (Japan, Mar. 1, 2012).
O'Brien MA, Moravec RA, Riss TL, Bulleit RF. Homogeneous, bioluminescent proteasome assays. Methods in molecular biology. 2015;1219:95-114.
Marshall NJ, Goodwin CJ, Holt Sj. A critical assessment of the use of microculture tetrazolium assays to measure cell growth and function. Growth regulation. 1995;5:69-84.
Zuang V. The neutral red release assay: a review. Alternatives to laboratory animals : ATLA. 2001;29:575-99.
Repetto G, del Peso A, Zurita JL. Neutral red uptake assay for the estimation of cell viability/cytotoxicity. Nature protocols. 2008;3:1125-31.
Franken NA, Rodermond HM, Stap J, Haveman J, van Bree C. Clonogenic assay of cells in vitro. Nature protocols. 2006;1:2315-9.
Rafehi H, Orlowski C, Georgiadis GT, Ververis K, El-Osta A, Karagiannis TC. Clonogenic assay: adherent cells. Journal of visualized experiments : JoVE. 2011.
Borenfreund E, Babich H, Martin-Alguacil N. Comparisons of two in vitro cytotoxicity assays—The neutral red (NR) and tetrazolium MTT tests. Toxicology in vitro : an international journal published in association with BIBRA. 1988;2:1-6.
Triglia D, Sherard Braa S, Yonan C, Naughton GK. Cytotoxicity testing using neutral red and MTT assays on a three-dimensional human skin substrate. Toxicology in vitro : an international journal published in association with BIBRA. 1991;5:573-8.
Lloyd M, Kidd D. The mouse lymphoma assay. Methods in molecular biology. 2012;817:35-54.

(Continued)

*Primary Examiner* — Bin Shen
(74) *Attorney, Agent, or Firm* — Sheng-Hsin Hu

(57) ABSTRACT

A cytotoxicity method for medical devices that has equivalent sensitivity, and greater efficiency compared to the colony formation assay (CFA) direct contact method is developed. The quantitative, direct contact cytotoxicity test method uses Mouse lymphoma TK or human lymphoblastoid TK6 suspension cells for medical device safety assessment. The advantages of using the suspension cell assay over adherent V79-4 cells is that this approach is quantitative, automated, not susceptible to potential mechanical damage imparted by the overlying test materials, and avoids issues related to non-adherence of cells to the test material which might impact the interpretation of test results.

13 Claims, 5 Drawing Sheets

(56) References Cited

OTHER PUBLICATIONS

Santodomingo-Rubido J, Mori O, Kawaminami S. Cytotoxicity and antimicrobial activity of six multipurpose soft contact lens disinfecting solutions. Ophthalmic & physiological optics : the journal of the British College of Ophthalmic Opticians. 2006;26:476-82.

International Organization for Standardization ISO 10993-12: 2012. Biological evaluation of medical devices—Part 12: Sample preparation and reference materials.

Tsuchiya T, Arai T, Ohhashi J, Imai K, Kojima H, Miyamoto S, et al. Rabbit eye irritation caused by wearing toxic contact lenses and their cytotoxicities: in vivo/in vitro correlation study using standard reference materials. Journal of biomedical materials research. 1993;27:885-93.

Puck TT, Marcus PI. Action of x-rays on mammalian cells. The Journal of experimental medicine. 1956;103:653-66.

Rodriguez RJ, Acosta D, Jr. N-deacetyl ketoconazole-induced hepatotoxicity in a primary culture system of rat hepatocytes. Toxicology. 1997;117:123-31.

Fellows MD, Luker T, Cooper A, O'Donovan MR. Unusual structure-genotoxicity relationship in mouse lymphoma cells observed with a series of kinase inhibitors. Mutation research. 2012;746:21-8.

Fischer GA. Studies of the culture of leukemic cells in vitro. Annals of the New York Academy of Sciences. 1958;76:673-80.

Honma M, Momose M, Sakamoto H, Sofuni T, Hayashi M. Spindle poisons induce allelic loss in mouse lymphoma cells through mitotic non-disjunction. Mutation research. 2001;493:101-14.

Zhang LS, Honma M, Hayashi M, Suzuki T, Matsuoka A, Sofuni T. A comparative study of TK6 human lymphoblastoid and L5178Y mouse lymphoma cell lines in the in vitro micronucleus test. Mutation research. 1995;347:105-15.

Matsushima T, Hayashi M, Matsuoka A, Ishidate M, Jr., Miura KF, Shimizu H, et al. Validation study of the in vitro micronucleus test in a Chinese hamster lung cell line (CHL/IU). Mutagenesis. 1999;14:569-80.

Von der Hude W, Kalweit S, Engelhardt G, McKiernan S, Kasper P, Slacik-Erben R, et al. In vitro micronucleus assay with Chinese hamster V79 cells—results of a collaborative study with in situ exposure to 26 chemical substances. Mutation research. 2000;468:137-63.

Erexson GL, Periago MV, Spicer CS. Differential sensitivity of Chinese hamster V79 and Chinese hamster ovary (CHO) cells in the in vitro micronucleus screening assay. Mutation research. 2001;495:75-80.

Carver JH, Salazar EP, Knize MG. Chinese hamster ovary cells cultured in low concentrations of fetal bovine serum: Cloning efficiency, growth in suspension, and selection of drug-resistant mutant phenotypes. In vitro. 1983;19:699-706.

Chiba K, Kawakami K, Tohyama K. Simultaneous evaluation of cell viability by neutral red, MTT and crystal violet staining assays of the same cells. Toxicology in vitro : an international journal published in association with BIBRA. 1998;12:251-8.

Munshi A, Hobbs M, Meyn R. Clonogenic Cell Survival Assay. Chemosensitivity. 2005;110:21-8.

\* cited by examiner

CYTOTOXICITY TEST METHOD FOR MEDICAL DEVICES

The invention relates to a method of using the suspension cells to quantitatively measure cytotoxicity for a medical device, such as a contact lens.

BACKGROUND OF THE INVENTION

The cytotoxicity testing is a primary requirement of all major standards for medical devices. It allows rapid evaluation, employs standard protocols, produces comparable data, and, due to its sensitivity, enables potentially toxic materials to be identified prior to in vivo testing. The high sensitivity of in vitro cytotoxicity tests compared to animal studies might be due to the direct exposure of cells to the material being tested and the absence of the protective mechanisms that assist cells in vivo. There are numerous screening cytotoxicity assays, whereas international health authorities and standard organizations focus on a more limited core test battery. Current recommendations or guidelines for medical device submission vary from quantitative (MTT/XTT, NR, and CFA) to qualitative assays (such as agar diffusion, direct contact, and elution test). With the continuous development in science and technology, new assays have evolved from qualitative to quantitative, thus one or more quantitative cytotoxicity assays are typically incorporated into the testing paradigm during the development of new devices.

Generally, three types of quantitative cytotoxicity assays are outlined in regulatory standards when evaluating materials for medical devices: (1) tetrazolium reduction (MTT/XTT); (2) neutral red (NR); and (3) colony formation (CFA). The MTT/XTT assay requires metabolically viable cells to convert a substrate to a colored product, whereas the NR assay is based on the lysosome membrane integrity of healthy cells. Both methods evaluate cell function using an automated UV/VIS plate reader to quantify the signals of colored products or dyes. The signal changes are a consequence of the adverse effects, which lead to dying cells rapidly losing the basal cell function (i.e., mitochondrial function, plasma membrane integrity). The cytotoxic effect is indicated by significant changes of cell functional activities compared with untreated controls, and thus indirectly measures the cell number. In contrast, the CFA monitors a cell's ability to produce a viable colony after treatment. Unlike the cell function assays (MTT/XTT and NR), the CFA is unbiased to the mode of cell death, since it directly measures the cytotoxic effect of a test material, regardless of mechanism, as long as the test material affects the cell's reproductive ability to form progenies. However, the CFA method using Chinese hamster lung fibroblast (V79) cells can be time consuming and because it is not automated, consistent objectivity is difficult to achieve when counting colonies manually under microscope.

One major difference between the two regulatory standards is that the quantitative method outlined in International Organization for Standardization (ISO) 10993-5 uses device extracts, while the Japan Ministry of Health, Labor and Welfare (JMHLW) guideline recommends using direct contact for devices whose leachables may be inactivated during the extraction process and for devices that come into direct contact with ocular tissues. In the CFA direct contact method, cells are either cultured on the surface of the medical device or, alternatively, the test material is placed directly on sparsely populated cultured cells. For devices on which adherent cells do not grow, such as contact lenses, the alternative method is required. In contrast, a different direct contact assay outlined in ISO, the agar diffusion/overlay, places the test material on a thin layer of agar overlaying mammalian cell monolayer. Each direct contact method has drawbacks. The disadvantages of using the agar layer are that it is a qualitative method, and potentially cytotoxic leachates may not be able to diffuse across the agar to fully expose the cultured cells. Although the direct contact CFA method is quantitative, the cells are more susceptible to potential mechanical damage by the overlying test materials. In addition, the measurement of the colony size is not included in the criteria for cytotoxicity evaluation in the ISO and JMHLW standards. For this reason, the direct contact CFA may not adequately capture the adverse effect of a test material exhibited by colonies that are smaller compared to control colonies but meet the test criteria of >50 cells/colony. Thus, there continues to be an important need for an automated quantitative method to assess cytotoxicity from direct contact with a test material using equally sensitive cell lines.

Due to the increased new types of medical devices to be evaluated, there is still need for automated, high-throughput screens that quantitatively assess cytotoxicity.

SUMMARY OF THE INVENTION

This invention is directed to a method of quantifying the cytotoxicity of a medical device, the method comprising: a) providing a medical device; b) incubating the medical device with suspension cells in culture medium; c) taking the images of the cells, d) determining the quantity of living cells using a cell counter with image analysis.

DETAILED DESCRIPTION

Figure 1:
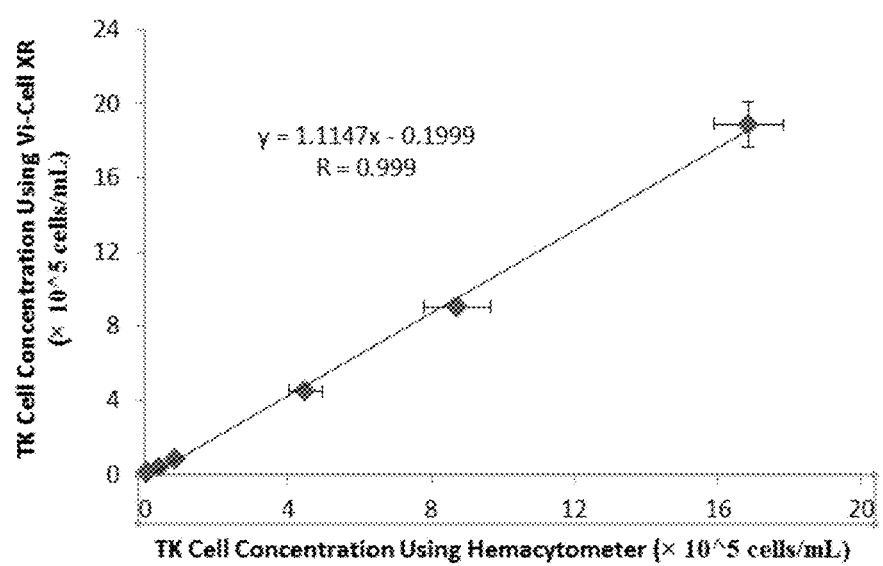
FIG. 1: Vi-Cell XR instrument parameter optimization. Mouse lymphoma thymidine kinase (TK) cells were grown in $RPMI_{10}$ medium to exponential phase. The cell numbers were quantified by either the Vi-Cell XR or a hemocytometer. The data represent the mean±SD of three replicates performed at each dilution and the correlation coefficient is indicated (R).

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

"Cells" are the building blocks of life because they make up all the tissues and parts of our bodies. Cells are herein used in its broadest sense in the art and refers to a living body which is a structural unit of tissue of a multicellular organism, is surrounded by a membrane structure which isolates it from the outside, has the capability of self-replicating, and has genetic information and a mechanism for expressing it. Cells used herein may be naturally-occurring cells or artificially modified cells (e.g., fusion cells, genetically modified cells, etc.).

"Medical device" refers to a device that is introduced temporarily or permanently into a mammal for the prophylaxis or therapy of a medical condition. For example, medical device may be a contact lens or these devices include any that are introduced subcutaneously, percutaneously or surgically to rest within an organ, tissue or lumen.

Medical devices may include stents, covered stents such as those covered with polytetrafluoroethylene (PTFE), or expanded polytetrafluoroethylene (ePTFE), synthetic grafts, artificial heart valves, artificial hearts and fixtures to connect the prosthetic organ to the vascular circulation, venous valves, abdominal aortic aneurysm (AAA) grafts, inferior venal caval filters, permanent drug infusion catheters, embolic coils, embolic materials used in vascular embolization (e.g., PVA foams), and vascular sutures. Medical devices may include scaffolds. Scaffolds are defined as three-dimension porous solid biomaterials designed to perform some or all of the following functions: (i) promote cell-biomaterial interactions, cell adhesion, and ECM deposition, (ii) permit sufficient transport of gases, nutrients, and regulatory factors to allow cell survival, proliferation, and differentiation, (iii) biodegrade at a controllable rate that approximates the rate of tissue regeneration under the culture conditions of interest, and (iv) provoke a minimal degree of inflammation or toxicity in vivo. The developing scaffolds with the optimal characteristics, such as their strength, rate of degradation, porosity, and microstructure, as well as their shapes and sizes, are more readily and reproducibly controlled in polymeric scaffolds. Polymer scaffolds can provide mechanical strength, interconnected porosity and surface area, varying surface chemistry, and unique geometries to direct tissue regeneration.

"Contact Lens" refers to a structure that can be placed on or within a wearer's eye. A contact lens can correct, improve, or alter a user's eyesight, but that need not be the case. A contact lens can be of any appropriate material known in the art or later developed, and can be a soft lens, a hard lens, or a hybrid lens. A "silicone hydrogel contact lens" refers to a contact lens comprising a silicone hydrogel material.

A "hydrogel" refers to a polymeric material which can absorb at least 10 percent by weight of water when it is fully hydrated. A hydrogel material can be obtained by polymerization or copolymerization of at least one hydrophilic monomer in the presence of or in the absence of additional monomers and/or macromers or by crosslinking of a prepolymer. A "silicone hydrogel" refers to a hydrogel obtained by copolymerization of a polymerizable composition comprising at least one silicone-containing vinylic monomer or at least one silicone-containing macromer or a silicone-containing prepolymer.

"Adherent cells", also called anchorage-dependent cells, are grown in cell culture medium while attached to the bottom of a tissue culture flask or other surface. Commonly, cells that come from tissue are considered to be adherent. When the cells are added to a tissue culture flask filled with cell culture medium and allowed to sit for about one day, they will begin to settle on the bottom and spread out. As they spread out, the cells secure a firm hold by adhering to the bottom surface of the flask.

"Suspension Cell", also called anchorage-independent cell, refers to a cell that can be grown by floating in the cell culture medium. When suspension cells are looked at under the microscope, they resemble tiny dots moving around in the liquid solution. There will be few or no clumps compared to in an adherent culture.

"Lymphoma TK Cells" refers to the mouse lymphoma TK assay (MLA) or human lymphoblastoid TK6 cells (both are commercially available from ATCC (American Type Culture Collection) which are used as a part of an in vitro battery of tests designed to predict risk assessment prior to in vivo testing. The test has the potential to detect mutagenic and clastogenic events at the thymidine kinase (tk) locus. cells.

"Marker" refers to biomarker as "a characteristic that is objectively measured and evaluated as an indicator of normal biological processes, pathogenic processes, or pharmacologic responses to a therapeutic intervention.

"Cell counter" Cell counters are tools for counting live and/or dead cells in a culture. Any researcher who works in a cell culture hood needs some sort of cell counting solution, whether to determine cell concentration prior to cell passage, or to assess cell viability following drug treatment. Both manual and automated cell counters are available. Manual cell counting is generally accomplished using a hemacytometer, a glass slide etched with a counting grid. Automated cell counters operate either via electrical impedance ("Electrical Sensing Zone" method), direct imaging (either on a disposable slide or in a flow chamber), or flow cytometry. The most important variable to consider in selecting a cell counting solution is the ability to assess cell viability. Electrical impedance (the Coulter Counting approach) generally cannot distinguish live from dead cells (except by size); but imaging-based approaches can, by using trypan blue to stain dead (but not live) cells, just as in classic hemacytometry.

The invention is generally directed to develop a new cytotoxicity method for medical devices that has equivalent sensitivity, and greater efficiency compared to the colony formation assay (CFA) direct contact method. The new, quantitative, direct contact cytotoxicity test method uses mouse lymphoma L5178Y thymidine kinase+/− (TK) suspension cells for medical device safety assessment. Mouse lymphoma L5178Y thymidine kinase+/− (TK) suspension cells are commercially available from American Type Culture Collection (ATCC) (Cat. #CRL-9518, ATCC, Manassas, Va.). The advantages of using the TK suspension cell assay over adhesion V79-4 cells is that this approach is quantitative, automated, not susceptible to potential mechanical damage imparted by the overlying test materials, and avoids issues related to non-adherence of cells to the test material which might impact the interpretation of test results. For the new method, assays were carried out in 24-well microplates; positive controls, negative controls, and six commercial contact lenses were used to assess the relative cell growth rate. Mouse lymphoma TK cells were seeded on top (concave side) of the lenses with a cell concentration of $2 \times 10^4$ cells/mL. Cell growth rate after 72 hours was determined using the Vi-Cell XR (Beckmann Coulter), and relative cell growth rate was calculated.

This method avoids the physical trauma caused by unintentional movement/pressure of the test material to the adhesion cells. Also, suspension cells can be easily cultured on the surface of the medical device, whereas the apparent colony forming ability of adhesion cells is decreased for a test material on which cells hardly adhere. Therefore the use of suspension mouse lymphoma TK cells appears promising for quantitative direct contact cytotoxicity studies.

This application provides a method of quantifying the cytotoxicity of a medical device, the method comprising: a) providing a medical device; b) incubating the medical device with suspension cells in culture medium; c) taking the images of the cells, d) determining the quantity of living cells using a cell counter with image analysis.

Material and Methods

The international standard cytotoxicity test reference materials A (polyurethane film containing 0.1% zinc diethyldithiocarbamate), B (polyurethane film containing 0.25% zinc dibutyldithiocarbamate), and C (high-density polyethylene sheet), were purchased from Hatano Research Institute (Hatano Research Institute, Food and Drug Safety Center, Hatano, Kanagawa, Japan). Wako tissue culture plastic disks were acquired from Wako Chemicals (diameter (φ): 14 mm, Cat. #162-09311, Richmond, Va.). Contact lenses representing six different commercial lens polymers were obtained from ABB Optical Group (Coral Springs, Fla.). The Vi-Cell assay kit (Cat. #383198) was purchased directly from Beckman Coulter (Brea, Calif.). All testing materials were freshly prepared prior to each experiment.

Mouse lymphoma TK cell culture medium. All the cell culture reagents were purchased from Thermo Fisher Scientific (Grand Island, N.Y.) unless stated otherwise. As previously described by Melvyn Lloyd 2012, the RPMI1640 medium (Cat. #11875), heat-deactivated horse serum (Cat. #26050), sodium pyruvate (Cat. #11360), pluronic F68 (Cat. #24040), and antibiotics were used in this study. The basic medium (designated $RPMI_0$) consisted of RPMI1640 medium supplemented with 200 µg/mL sodium pyruvate, 0.5 mg/mL pluronic F68, 100 U/mL penicillin and 100 µg/mL streptomycin (Cat. #15140). Growth media (designated $RPMI_{10}$) was $RPMI_0$ with 10% (v/v) heat-deactivated horse serum. The TK cells assay medium was $RPMI1640_0$ supplemented with either 10% (v/v) fetal bovine serum (FBS, Cat. #26140) or 5% (v/v) FBS and designated as $RPMI_{FBS10}$ and $RPMI_{FBS05}$ respectively.

Mouse Lymphoma TK Cell Culture and Maintenance

The mouse lymphoma L5178Y $TK^{-/-}$ clone (3.7.2C) was obtained from American Type Culture Collection (ATCC) (Cat. #CRL-9518, ATCC, Manassas, Va.) and expansively cultured to make master stocks (within 30 passages). Master stocks were maintained in liquid nitrogen at a density of $2 \times 10^6$ cells/mL with growth media containing 5% dimethylsulfoxide (DMSO) (Cat. #D2650, Sigma-Aldrich, St. Louis, Mo.). They were confirmed as free from mycoplasma by ATCC. After thawing, mouse lymphoma TK cells were grown at 37° C. with a humidified atmosphere of 5% (v/v) carbon dioxide ($CO_2$) in air to achieve logarithmic growth. The cells were routinely diluted to $\sim 2 \times 10^5$ cells/mL confirmed by either a hemocytometer or Vi-Cell XR to prevent overgrowth ($>2 \times 10^6$ cells/mL) in growth media and were used after two weeks of passage and during logarithmic growth.

Data Analysis

For each test material, data were collected and the mean and SD were calculated using Excel. The $IC_{50}$ was calculated using SigmaPlot. Determination of cytotoxicity and test acceptance criteria followed those described in JMHLW and ISO 10993-5: The relative colony-forming rate/relative growth rate of positive control (reference material B) should be equal or less than 10%, and negative control (Wako disk) should be equal or greater than 80%. A test material was considered cytotoxic in the assay if the relative colony formation rate/relative grow rate is less than 30% as compared to the blank control and was considered negative if it did not satisfy the above mentioned criteria.

Example 1: Vi-Cell XR Instrument Parameter Optimization

The Beckman Coulter Vi-Cell XR (Beckman Coulter, Indianapolis, Ind.) is an automatic cell counter combined with Trypan Blue dye as a marker of cytotoxicity, which penetrates the cell membranes of dead cells with a characteristic blue color and leads to easy differentiation of live (no blue color) and dead (blue) cells. Using the Vi-Cell XR with video capture technology (Vi-Cell XR Cell Viability Analyzer Software version 2.03), a cell sample was taken and delivered to the flow cell for imaging. Cells vary in their optical characteristics; therefore the optical settings are important to correctly identify and quantify viable versus non-viable cells. In this assay, the Vi-Cell XR was set to capture 100 images per sample with the maximum cell size set as 20 micron and the minimum cell size set as 6 micron to exclude cellular debris. Three cycles of both the aspirate and Trypan Blue mixing were used to keep a single cell suspension and achieve good mixing. The cell brightness (70%) and sharpness (100) were optimized to determine whether the boundary "dark" pixels belonged to a cell or were part of the background. The viable cell spot brightness (75%) and area (5%) were used to determine whether a cell was viable or non-viable. Minimum circularity was set as 0.8 to reject debris that exceeded the minimum cell diameter but was too irregularly shaped to be treated as a viable cell. Validation of the parameter optimization is described as follows:

An important criterion for developing sensitive and reliable in vitro assays is the proper instrument parameter set up. To confirm the optimization of the Vi-Cell XR parameters, we performed a serial dilution of TK cells ($2\times10^6$, $1\times10^6$, $5\times10^5$, $1\times10^5$, $5\times10^4$, and $1\times10^4$ cells/mL) and then the cell density was determined with either a hemacytometer or the Vi-Cell cell counter. The results (FIG. 1) showed that the readings from both the Vi-Cell XR and hemacytometer increased linearly with increasing numbers of cells, and the correlation of the results from hemocytometer and Vi-Cell XR was very strong (R=0.999). Thus, the parameters for Vi-Cell XR were optimized to accurately quantify TK cell numbers at range of $1\times10^4$ to $2\times10^6$ cells/mL.

Example 2: Effect of Contact Lenses on Growth of Mouse Lymphoma TK Cells in the TK Suspension Cell Assay Assays were carried out in 24-well microplates (Cat. #3526, Corning, Corning, N.Y.). To mimic real life situations, each contact lens was removed from the saline in the manufacturer's package and placed without blotting directly into each well of the 24-well plate containing 500 μL RPMI$_{FBS10}$ assay media. TK cells were collected and reseeded (500 μL, $4\times10^4$ cells/mL) on the concave surface of the lens with a cell concentration of $2\times10^4$ cells/mL. Non-treated cells served as the blank control, reference material B (diameter (ϕ): 14 mm) was the positive control, and Wako disk was the negative control. After 72±2 hours of incubation, 600 μL cells were mixed and transferred into the cell counter vial. The cell growth rate after 72 hours was determined using the Vi-Cell XR, and relative cell growth rate was calculated using the following equation:

Relative cell growth rate (%)=[100×(Test cell concentration at time 72 hours−mean of blank cell concentration at time 0)÷(mean of blank cell concentration at time 72 hours−mean of blank cell concentration at time 0)]. The results are expressed as the mean±standard deviation (SD) from three independent studies and each study has six replicates for each lens.

Figure 2A:
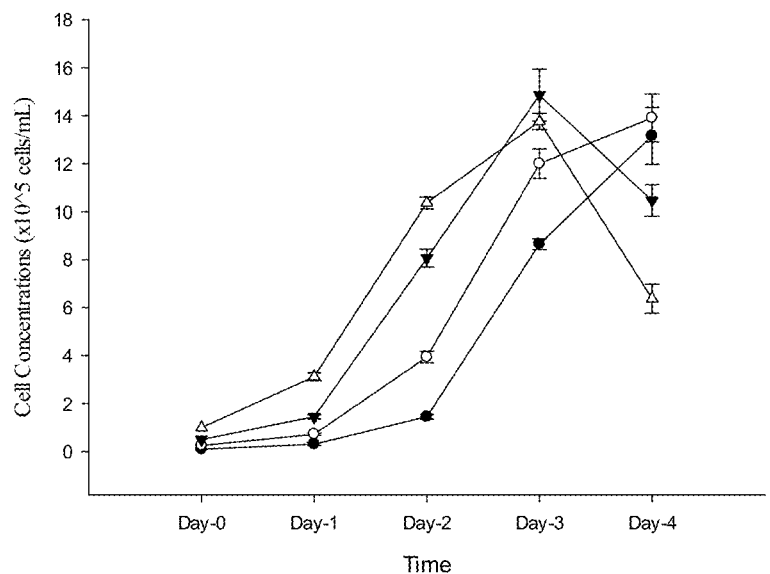
FIGS. 2A-2B: Mouse lymphoma TK cell growth rate. Cells were seeded at $1\times10^4$ cells/mL (● closed circle), $2.5\times10^4$ cells/mL (○ open circle), and $5\times10^4$ cells/mL (▲ closed triangle), and $1\times10^5$ cells/mL (Δ open triangle). A) Mouse lymphoma TK cell growth rate using 5% fetal bovine serum (FBS). B) Mouse lymphoma TK cell growth rate using 10% FBS. The data represent the means from six replicates at each dilution, with the bars showing standard deviation.

In addition to instrument parameter optimization, another important criterion for cell growth inhibition assays is that the cells should be at the logarithmic growth phase during the treatment. The TK cell numbers were quantified by Vi-Cell XR, serial dilutions were prepared, and seeding concentrations between $1\times10^4$ and $1\times10^5$ cells/mL were used per assay with six replicates. Then the TK cells were harvested and quantified at 0, 24, 48, 72, and 96 hours to generate the cell growth curve. Since the doubling time for TK cells is 9-11 hours, the 72-hour incubation time was chosen for the final assay so that the TK cells could undergo at least 6 divisions. This is consistent with the CFA using V79 cells, in which a colony is defined to consist of at least 50 cells, which are formed after about 6 cell divisions. Our data showed that both $1\times10^4$ cells/mL and $2.5\times10^4$ cells/mL TK cells were grown to exponential phase for 72 hours incubation (FIGS. 2A and B). The TK cell number at $1\times10^5$ cells/mL was significantly decreased on day 4 at 5% FBS, which might be due to the deficiency of nutrient as compared to the 10% FBS. The standard error between replicates was slightly higher at $1\times10^4$ cells/mL at earlier time points, which might be due to the cell concentration being below the Vi-Cell XR detection limit ($5\times10^4$ cells/mL) (data not shown). Therefore, a seeding concentration at $2\times10^4$ cells/mL was employed for the studies. Since most of the historical data for positive and negative controls in CFAs used FBS, the mouse lymphoma TK cell ($2\times10^4$ cells/mL) growth rates were further tested using different kinds of serum (Table 1). Our data showed that FBS and horse serum had a similar impact on TK cell growth rate.

TABLE 1

Mouse Lymphoma TK Cells Growth Rates Using Different Kinds of Serum

| TK Growth Medium | Cell Concentrations ($\times10^5$ cells/mL)$^a$ | |
|---|---|---|
| | Time 0 | Time 72 hours |
| 5% Horse Serum RPMI1640 | 0.19 ± 0.04 | 16.62 ± 0.87 |
| 5% Fetal Bovine Serum RPMI1640 | 0.24 ± 0.05 | 14.92 ± 0.44 |
| 10% Horse Serum RPMI1640 | 0.18 ± 0.02 | 18.70 ± 1.38 |
| 10% Fetal Bovine Serum RPMI1640 | 0.23 ± 0.02 | 18.48 ± 0.70 |

$^a$Data represent the mean ± SD from six replicates for each sample.

Example 3: Effect of Contact Lenses on Colony Formation of V79 Cells in the CFA Direct Contact Method Testing was performed according to the JMHLW standard. Chinese hamster lung cells, V79-4 (Cat. #CCL-93, ATCC, Manassas, Va.) were propagated and maintained in M10 (single-strength Eagle's Minimum Essential Medium with Earle's balanced salt solution (Cat. #SH30024.01, HyClone, Logan, Utah) supplemented with 10% certified FBS at 37.0° C. in a gaseous environment of 5.0% $CO_2$. Briefly, V79 cell suspension after trypsinization was diluted to 100 cells/mL and then 500 μL of cell suspension was added into the 24-well plate containing 500 μL of medium (M10). The culture was incubated overnight at 37° C., allowing the cells to attach to the base of the plate. After incubation, the contact lenses were added directly into each well (concave up). Non-treated cells served as blank control, reference material B (diameter (ϕ): 14 mm) was the positive control, and Wako tissue culture plastic disk was the negative control. After an additional 6 days of culture, contact lenses were carefully removed; the cells were fixed with methanol (Cat. #BDH20864, VWR, Suwanee, Ga.) and stained with 2% Giemsa solution (Cat. #10092, ThermoFisher Scientific, Grand Island, N.Y.). The number of colonies with 50 cells or more was manually counted using a Vista Vision microscope (2×). The results are expressed as the mean±SD based on six replicates per lens.

Figure 2B:
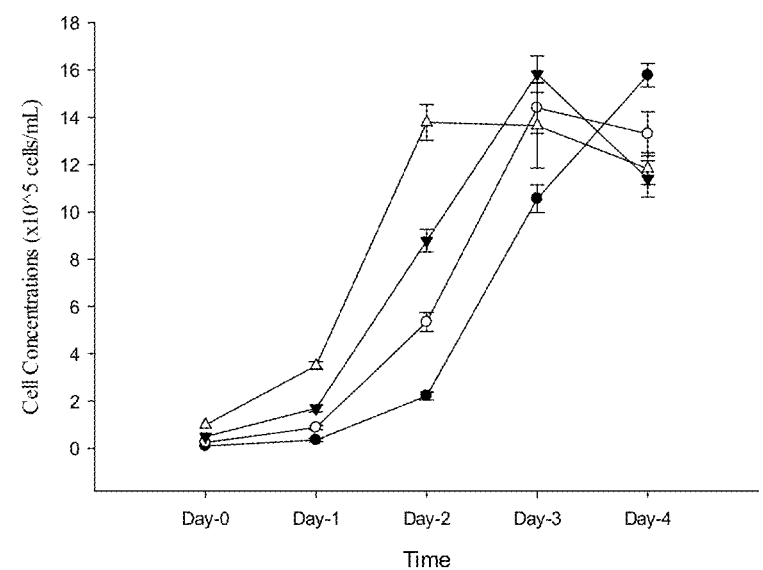
Figure 3A:
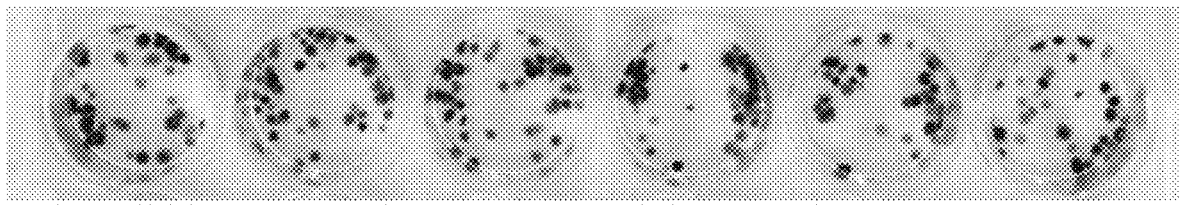
FIGS. 3A-3E: Direct contact colony formation assay. Fifty V79 cells were seeded and allowed to attach to the bottom in each well. Contact lenses were placed on top in close contact with the V79 cells. On day 7 after seeding, contact lenses were removed and cells were fixed and stained to determine colony formation rates. A) Blank. B) Positive control—reference material B. C) Negative control—wako disk. D) Senofilcon A contact lens. E) Polymacon contact lens. The data represent six replicates.
Figure 3B:
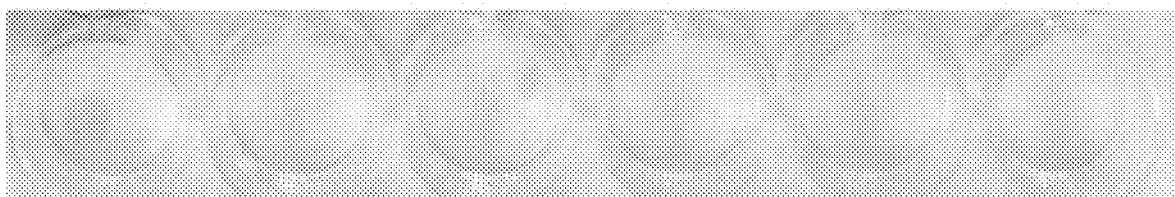
Figure 3C:
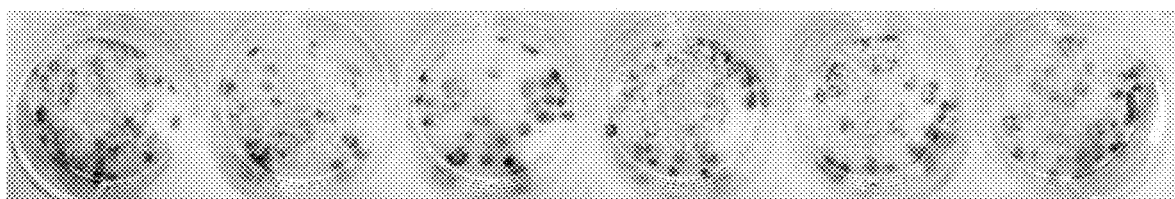
Figure 3D:
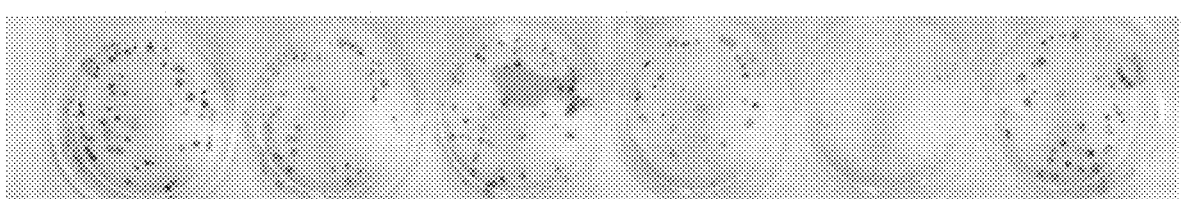
Figure 3E:
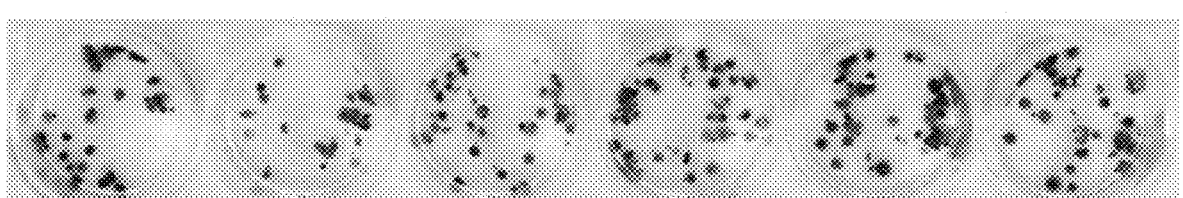

Both positive control (reference material B) and negative control (Wako disk) using the TK suspension cell assay showed similar results as compared to the Japan direct contact CFA (Table 3). In addition, our data demonstrated an 83.0% correlation between the TK suspension cell assay and the CFA direct contact method in five of six commercial contact lenses studied. Although the difference in incubation time might raise concerns about consistency with the CFA results, our data demonstrate that those theoretical concerns do not raise any practical issues with this assay. Senofilcon A lenses showed a higher colony formation rate (79.0±9.8%) in the CFA direct contact assay compared to the cell growth rate (17.1±4.6%) using the mouse TK cells. This inconsistency might be due to the fact that colony sizes treated with senofilcon A were much smaller as compared to the blank control, which might be an indication of a cytotoxicity effect (FIG. 2). Since there is no cytotoxicity evaluation criterion for colony size in the CFA, the mouse lymphoma TK cell growth inhibition assay might be a more sensitive approach due to its measurement of the total viable cells.

TABLE 2

Results of Direct Contact Assay Using Mouse Lymphoma TK Suspension Cell Assay Versus CFA with V79 Cells.

| Test articles | Mouse Lymphoma TK Relative growth rate compared to blank (%)[b] (Mean ± STD) | CFA with V79 Cells Relative colony formation rate (%) - direct contact method[b] (Mean ± STD) |
|---|---|---|
| Reference Materials | | |
| Positive - reference material B | −0.5 ± 0.7 | 0 ± 0 |
| Negative - Wako | 89.4 ± 9.5 | 94.4 ± 10.9 |
| Contact Lenses[a] | | |
| Etafilcon A | 10.3 ± 2.4 | 29.6 ± 9.6 |
| Galyfilcon A | 13.9 ± 1.4 | 18.1 ± 8.7 |
| Senofilcon A | 17.1 ± 4.6 | 79.0 ± 9.8[c] |
| Balafilcon A | 2.3 ± 3.1 | 3.5 ± 8.5 |
| Methafilcon A | 89.9 ± 11.1 | 91.3 ± 12.8 |
| Polymacon | 61.2 ± 18.5 | 83.5 ± 10.9 |

[a]Contact lenses were removed from the package saline and used without blotting.
[b]Data represent the mean ± SD from three independent studies and each study has six replicates for each lens.
[c]Smaller colony size compared to blank.

Example 4: Effect of Benzalkonium Chloride (BAK) and ZDBC on Growth of Mouse Lymphoma TK Cells in the TK Suspension Cell Assay Phosphate buffer (Cat. #SH30028.02, HyClone, Logan, Utah) was used for dilutions of BAK (1.25, 2.5, 5, 10, 25, and 50 parts per million) (Cat. #B1068, Spectrum Chemical, New Brunswick, N.J.). A total of 900 μL of 2.2×10$^4$ cells/mL TK cells in assay medium (RPMI$_{FBS10}$ or RPMI$_{FBS05}$) were seeded in a 24-well plate and then treated with different dilutions of BAK (100 μL) to achieve final concentrations of 0.125, 0.25, 0.5, 1.0, 2.5, and 5 ppm. Phosphate buffer (100 μL)-treated cells served as a blank control, reference material B (diameter (φ): 14 mm) as a positive control, and Wako tissue culture plastic disk served a negative control. After 72±2 hours incubation, 600 μL cells were mixed and transferred into the counter vial. The relative cell growth rate was determined and calculated as described above. The results are expressed as the mean±SD based on three replicates.

DMSO was used to dissolve ZDBC powder (Cat. #Z1031, Spectrum Chemical, New Brunswick, N.J.) to make 0.05, 0.1, 0.2, 0.4, 0.8, and 2 mg/mL dilutions. Next, 995 μL of 2.0×10$^4$ cells/mL TK cells in assay medium (either RPMI$_{FBS10}$ or RPMI$_{FBS05}$) were seeded in a 24-well plate and treated with 5 μL of different ZDBC dilutions to achieve final concentrations of 0.25, 0.5, 1, 2, 4, and 10 μg/mL. DMSO (5 μL)-treated cells served as a blank control, reference material B (diameter (φ): 14 mm) as a positive control, and Wako tissue culture plastic disk served a negative control. After 72±2 hours incubation, 600 μL cells were mixed and transferred into the counter vial. The relative cell growth rate was determined and calculated as described above. The results are expressed as the mean±SD based on three replicates.

Figure 4A:
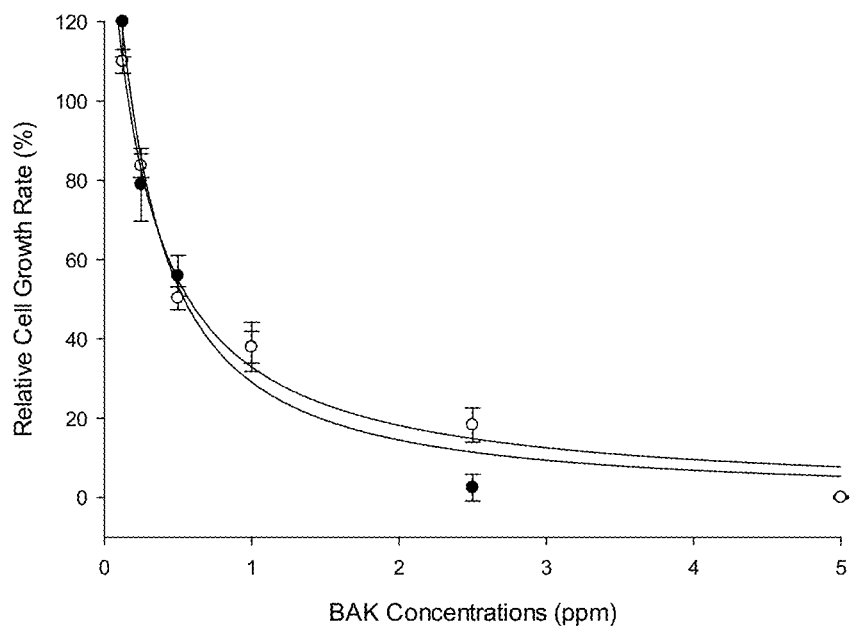
FIGS. 4A-4B: Effect of benzalkonium chloride (BAK) and zinc dibutyldithiocarbamate (ZDBC) on relative growth rate of mouse lymphoma TK cells. A) Mouse lymphoma TK cells were treated with serial dilutions of BAK for 72±2 hours with either 5% FBS (● closed circle) 10% FBS (○ open circle). B) Mouse lymphoma TK cells were treated a serial dilutions of ZDBC for 72±2 hours with either 5% FBS (● closed circle) 10% FBS (○ open circle). The data represent the mean of three replicates performed at each dilution, with the bars showing standard deviation.
Figure 4B:
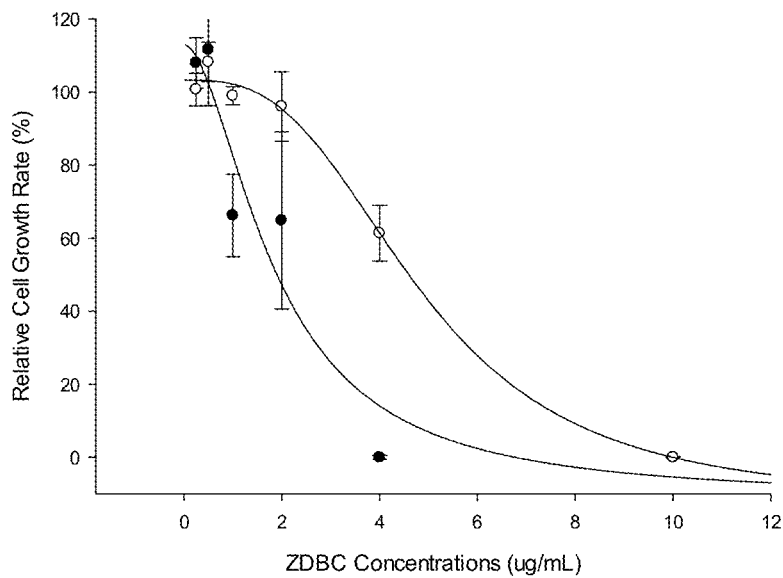

BAK and ZDBC both showed a dose-dependent decrease in cell growth. BAK at 5, 2.5, 1, and 0.5 ppm yielded significant cell growth inhibition as compared to the blank control. Both 0.25 and 0.125 ppm BAK were not cytotoxic (FIG. 4A). The 5% FBS (BAK: IC$_{50}$=0.55 ppm) and 10% FBS (BAK: IC$_{50}$=0.59 ppm) did not have any impact on cytotoxicity for BAK treatment. ZDBC showed lower IC$_{50}$ using the 5% FBS medium (IC$_{50}$=2.0 μg/mL) as compared to the 10% FBS medium (IC$_{50}$=4.5 μg/mL) (FIG. 4B), which is consistent with the reference results in the JMHLW standard.

Example 5: Effect of Reference Material Extracts on Growth of Mouse Lymphoma TK Cells in the TK Suspension Cell Assay Assays were carried out in 6-well plates (Cat #3506, Corning, Corning, N.Y.). Each extraction was prepared according to ISO 10993-12 (2012) and JMHLW standards. Briefly, reference materials A, B, and C were extracted (reference materials A and B, 0.1 g/mL; reference material C, 0.2 g/mL) using assay medium (RPMI$_{FBS10}$ or RPMI$_{FBS05}$) for 24 hours at 37° C. Each extraction of reference materials was further diluted using assay medium (RPMI$_{FBS10}$ or RPMI$_{FBS05}$). Three (3) mL of reference material A (2%, 1%, 0.5%, 0.25% and 0.125%), reference material B (100%, 75%, 50%, 25%, and 12.5%), or reference material C (100%) dilutions were added into wells of a 6-well plate. Cells were collected and reseeded (30 μL, 2×10$^6$ cells/mL) into each well. After 72±2 hours incubation, 600 μL cells were mixed and transferred into the counter vial. The relative cell growth rate was calculated as described above. The results are expressed as the mean±SD on three replicates.

Figure 5A:
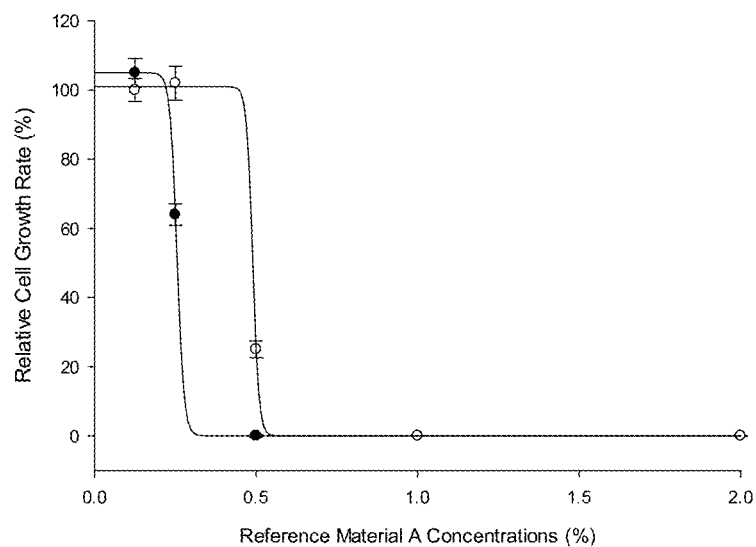
FIGS. 5A-5B: Effect of extracts of the reference material A and B on relative growth rate of mouse lymphoma TK cells. Mouse lymphoma TK cells were treated with different concentrations of reference material A and B for 72±2 hours. A) Reference material A (5% FBS ● closed circle; 10% FBS ○ open circle). B) Reference material B (5% FBS ● closed circle; 10% FBS ○ open circle). The data represent the mean of three replicates performed at each dilution, with the bars showing standard deviation.
Figure 5B:
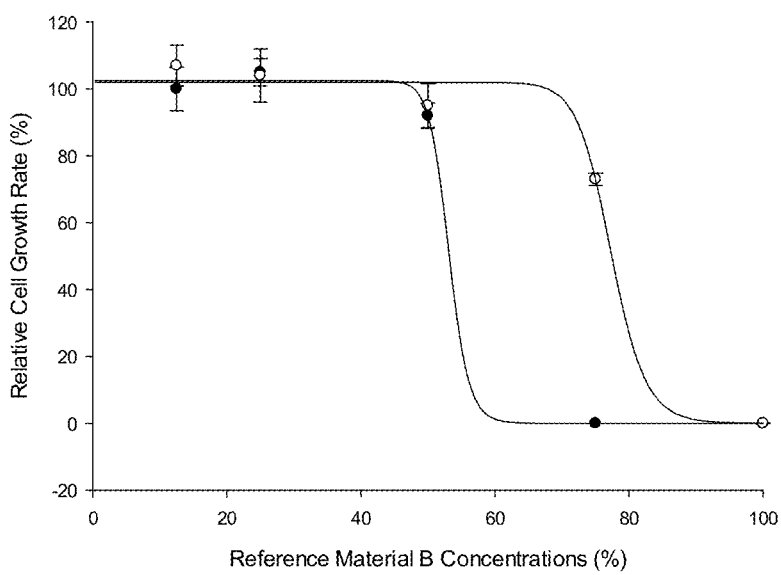

The 100% extract of reference material C did not have any impact on the relative cell growth rate (5% FBS: 89%±10%; 10% FBS 100%±9%). The extract of reference material A was significantly more cytotoxic than that of reference material B, and both behaved in a dose-dependent manner (FIGS. 5A and 5B). In addition, both reference material A (5% FBS: IC50=0.26%; 10% FBS: IC50=0.49%) and reference material B (5% FBS: IC50=53%; 10% FBS: IC50=78%) had lower IC$_{50}$ using 5% FBS medium as compared to 10% FBS medium, which is also consistent with the reference results in the JMHLW standard.

DISCUSSION AND CONCLUSIONS

Cytotoxicity testing is an important endpoint for biological safety evaluations of medical devices and provides a standardized, sensitive, and inexpensive means to determine whether a test material contains significant quantities of potentially biologically harmful leachables. The results obtained from cytotoxicity test systems have indicated that the relative toxicity can vary not only according to exposure time, cultured cell type, and presence or absence of serum, but also by the choice of endpoints. There are a variety of assay technologies ranging from qualitative to quantitative that utilize the device or its extracts as the test material to estimate the cell viability following direct contact. Each cell viability assay has its own set of advantages and disadvantages (Table 3). Regardless of the assay method chosen, the major critical factors for reproducibility and accuracy include: (1) using a tightly controlled, well characterized, and consistent source of cells, and (2) performing appropriate characterization of reagent concentration and incubation time for each experimental model system.

TABLE 3

Comparison of Mouse Lymphoma TK and Current Quantitative Cytotoxicity Testing Method

| | | |
|---|---|---|
| Assays | TK Suspension Cell Assay | JMHLW Colony Formation Direct Contact |
| Cell line | L5178Y thymidine kinase+/− (TK) | V79 |
| Cell type | Mouse Lymphoma | Chinese hamster lung fibroblast cells |
| Cell characteristics | Well characterized suspension cells | Well characterized adhesion cells |
| Treatment time | 72 hours | 6-7 days |
| Measurement | Quantitative/Number of viable cells | Quantitative/Number of colonies |
| Assay mechanism | Cell growth | Cell growth |
| Instrument | Cell Counter | Manually count |
| Automation | Yes | No |
| Test material | Direct contact and medical device extract. | Direct contact and medical device extract. |
| Method criteria | Direct: A test material is considered cytotoxic in the assay if the relative grow rate is less than 30% as compared to the blank control. Extract: The test material is judged as cytotoxic if the relative grow rate in the 100% test solution shows a decrease beyond 30% of the rate in the blank control group. | Direct: The test material is judged as cytotoxic when the $IC_{50}$ is 100% or lower in the extraction method and the colony formation rate of the direct contact method is less than 30%. Extract: The test material is judged as cytotoxic when the colony formation rate in the 100% test solution shows a decrease beyond 30% of the rate in the blank control group (the colony formation rate <70%). |
| Advantages | Quantitative, automated, and not susceptible to potential mechanical damage imparted by the overlying test materials, and avoids issues related to non-adherence of cells to the test material. | Quantitative, direct measurement of cell growth. More historic data No special equipment needed |
| Disadvantages | Special equipment needed Need further validation and characterization | Labor intensive; potential mechanical damage by overlying test materials, and adhesion cells might not grow on the surface of the medical device. Only one side of the material can be evaluated. |
| Assays | ISO - Agar Overlay | ISO - Direct Contact |
| Cell line | L-929 | L-929 |
| Cell type | Mouse fibroblastic cell | Mouse fibroblastic cell |
| Cell characteristics | Well characterized adhesion cells | Well characterized adhesion cells |
| Treatment time | 24 hours | 24 hours |
| Measurement | Qualitative | Qualitative |
| Assay mechanism | Cytotoxicity | Cytotoxicity |
| Instrument | Microscope | Microscope |
| Automation | No | No |
| Test material | Indirect contact with test material | Direct contact |
| Method criteria | The biological reactivity is rated on a scale of 0-4. The test material is judged as not cytotoxic if the response is not greater than grade 2. | The biological reactivity is rated on a scale of 0-4. The test material is judged as not cytotoxic if the response is not greater than grade 2. |
| Advantages | Avoid mechanical damage by overlying test materials. More historic data No special equipment needed | Direct contact with cells. More historic data No special equipment needed |
| Disadvantages | Qualitative and cytotoxic leachates may not be able to diffuse across the agar to fully expose the cultured cells. Only one side of the material can be evaluated. | Qualitative and potential mechanical damage by overlying test materials. Only one side of the material can be evaluated. |

Although MTT/XTT and NR assays are used extensively as convenient, sensitive, and rapid measures of cell viability, each of the method has their disadvantages and must be used with caution. For example, reducing agents and respiratory chain inhibitors could potentially affect the MTT formazan formation of mitochondrial MTT reduction in the MTT/XTT assay. In terms of the NR assay, an increase in NR uptake was demonstrated to have been induced by lysosomal swelling agents such as weakly basic substances and by osmotic swelling agents such as polyols. The lysosomal swelling may lead to an underestimation of the cytotoxicity when the NR assay is used. The mouse lymphoma TK suspension cell assay we described here directly monitors a cell's ability to propagate after treatment using the video capture imaging technology. Our goal was to develop a cell proliferation assay with direct contact to a medical device using automated technology, thereby increasing efficiency in performing large-scale, reproducible experiments. This new method uses an automatic cell counter combined with Trypan Blue dye as a marker of cytotoxicity, which penetrates the cell membranes of dead cells with a characteristic blue color and leads to easy differentiation of live (no color) and dead (blue) cells. While there are a number of cell lines that can be used, the mouse lymphoma TK cell line is preferred based on a body of research that exists for this cell line. It is commonly used in a standard in vitro mammalian gene mutation assay and has the ability to grow in suspension. Chinese hamster lung (V79) and ovary (CHO) cells, used in CFAs, were also used in in vitro mammalian gene mutation assays use. The quantitative cell function assays (MTT/XTT and NR) are using biochemical methods to indirectly measure the inhibition of cell growth. The effects on cell function are a consequence of non-specific alternations in "basic cell functions" (i.e., mitochondria, plasma membrane integrity, etc.), which may then lead to impairment or death of the cell. Since these are early cellular changes, the lethality or reversibility of the effect may be unknown. The new TK suspension cell assay is unbiased to the mode of cell death and is able to detect the cytotoxic effect of a test material, regardless of mechanism. Another advantage of this approach is the ability to seed TK cells on top of the test materials, which achieves direct contact without physical trauma to seeded cells and avoids confounding effects when cells are not able to adhere to the test material. Cell density and cytotoxicity are easily determined using a cell counter combined with the Trypan Blue stain. Furthermore, this TK method is more sensitive as compared to the CFA direct contact which reports only colony number and does not include the colony size in the criteria for cytotoxicity evaluation as long as there are more than 50 cells per colony. This feature may mask the adverse effect exhibited by smaller colonies in test materials.

In summary, data demonstrate that this TK suspension cell assay using the L5178 TK$^{+/-}$–3.7.2.C mouse lymphoma cell line performs equivalently in determination of potential cell growth inhibition to the direct contact colony formation assay described in several regulatory standards. This method represents a valuable addition to the battery of assays for detection of potentially toxic materials leaching from a test material that is either a solid or liquid. Further work would be required to focus on large-scale and formal validation, which would provide more information about the criteria applied in this assay and prove its applicability for medical device safety assessment.

The invention has been described with the aid of a specific embodiment of the process or apparatus, respectively. However, the invention is not limited to the specific embodiment described but rather various changes and modifications are possible without departing from the general concept underlying the invention. Therefore, the scope of protection is defined by the appended claims.

What is claimed is:

1. A method of quantifying the cytotoxicity of a medical device, the method comprising: a) providing a medical device; b) incubating the medical device with suspension cells in culture medium for growing the suspension cells; c) taking the images of the cells, d) determining the quantity of living cells using a cell counter with image analysis, wherein the suspension cells are mouse lymphoma thymidine kinase (TK) or human lymphoblastoid lymphoma thymidine kinase 6 (TK6) cells.

2. The method of claim 1, wherein the suspension cells are Mouse lymphoma TK cells.

3. The method of claim 1, wherein a reagent of the culture medium is select from a group consisting of heat-deactivated horse serum, sodium pyruvate, a non-ionic surfactant with a polyoxypropylene molecular mass of 1800 g/mol and a 80% polyoxyethylene content (pluronic F68) and combination thereof.

4. The method of claim 1, wherein the step of d) determining the quantity of living cells is to use a cell counter with image analysis cells based on the cell size, circularity, brightness, or shape.

5. The method of claim 1, further comprising the steps of labeling the cells with a dye.

6. The method of claim 5, further comprising the steps of detecting the labelled cells.

7. The method of claim 6, wherein the incubating in step (b) is effected in a 6, 24 or 96-multi-well plate.

8. The method of claim 5, wherein the dye is Trypan Blue.

9. The method of claim 1, wherein the incubating in step (b) is effected in a multi-well plate.

10. The method of claim 1, wherein the medical device is a contact lens.

11. The method of claim 1, wherein the medical device is a stent.

12. The method of claim 1, wherein the medical device is a scaffold.

13. The method of claim 1, wherein the medical device is an implant.

* * * * *